(12) United States Patent
Sue et al.

(10) Patent No.: US 8,038,661 B2
(45) Date of Patent: Oct. 18, 2011

(54) ABSORBENT ARTICLE WITH LOW COLD FLOW CONSTRUCTION ADHESIVE

(75) Inventors: Shunketsu Sue, Mason, OH (US);
Ebrahim Rezai, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 429 days.

(21) Appl. No.: 11/512,773

(22) Filed: Aug. 30, 2006

(65) Prior Publication Data
US 2007/0055211 A1    Mar. 8, 2007

Related U.S. Application Data

(60) Provisional application No. 60/714,188, filed on Sep. 2, 2005.

(51) Int. Cl.
*A61F 13/15*     (2006.01)

(52) U.S. Cl. .............. 604/385.03; 604/367; 604/385.04; 604/385.05; 604/386; 604/387; 604/389; 604/366

(58) Field of Classification Search ............. 604/385.03, 604/385.04, 385.05, 386, 387, 389, 366, 604/367
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Peterson |
| 3,502,763 A | 3/1970 | Hartmann |
| 3,542,615 A | 11/1970 | Hartmann |
| 3,692,618 A | 9/1972 | Dorschner et al. |
| 3,802,817 A | 4/1974 | Matsuki et al. |
| 3,848,594 A | 11/1974 | Buell |
| 3,849,241 A | 11/1974 | Butin et al. |
| 3,860,003 A | 1/1975 | Buell |
| 3,860,003 A | 1/1975 | Buell |
| 3,860,003 A | 1/1975 | Buell |
| 4,340,563 A | 7/1982 | Appel et al. |
| 4,610,678 A | 9/1986 | Weisman et al. |
| 4,662,875 A | 5/1987 | Hirotsu et al. |
| 4,662,875 A | 5/1987 | Hirotsu et al. |
| 4,699,622 A | 10/1987 | Toussant et al. |
| 4,808,178 A | 2/1989 | Aziz et al. |
| 4,834,735 A | 5/1989 | Alemany et al. |
| 4,846,815 A | 7/1989 | Scripps |
| 4,888,231 A | 12/1989 | Angstadt |

(Continued)

FOREIGN PATENT DOCUMENTS

EP    A-0-531 618    3/1993

(Continued)

OTHER PUBLICATIONS

Written Opinion of the International Searching Authority, Application No. PCT/IB2006/053075, dated Mar. 4, 2008.

*Primary Examiner* — Jacqueline F. Stephens
(74) *Attorney, Agent, or Firm* — Amy M. Foust; Richard L. Alexander; Eric T. Addington

(57) ABSTRACT

Absorbent articles assembled using a low cold flow construction adhesive are described. The absorbent articles have an in bag compression opening force of less than about 0.75N. A method for making the absorbent articles is also described.

30 Claims, 2 Drawing Sheets

U.S. PATENT DOCUMENTS

| | | | |
|---|---|---|---|
| 4,892,536 A | 1/1990 | Desmarais et al. | |
| 4,894,060 A | 1/1990 | Nestegard | |
| 4,909,803 A | 3/1990 | Aziz et al. | |
| 4,940,464 A | 7/1990 | Van Gompel et al. | |
| 4,946,527 A | 8/1990 | Battrell | |
| 4,963,140 A | 10/1990 | Robertson et al. | |
| 4,990,147 A | 2/1991 | Freeland | |
| 5,037,416 A | 8/1991 | Allen et al. | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell et al. | |
| 5,213,881 A | 5/1993 | Timmons et al. | |
| 5,221,274 A | 6/1993 | Buell et al. | |
| 5,242,436 A | 9/1993 | Weil et al. | |
| 5,246,433 A | 9/1993 | Hasse et al. | |
| 5,260,345 A | 11/1993 | Desmarais et al. | |
| 5,269,775 A | 12/1993 | Freeland et al. | |
| 5,342,338 A | 8/1994 | Roe | |
| 5,387,207 A | 2/1995 | Dyer et al. | |
| 5,397,316 A | 3/1995 | Lavon et al. | |
| 5,499,978 A | 3/1996 | Buell et al. | |
| 5,507,736 A | 4/1996 | Clear et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,744,538 A * | 4/1998 | Miller et al. | 524/539 |
| 5,865,823 A | 2/1999 | Curro | |
| 5,897,545 A | 4/1999 | Kline et al. | |
| 5,957,908 A | 9/1999 | Kline et al. | |
| 6,004,306 A | 12/1999 | Robles et al. | |
| 6,087,550 A * | 7/2000 | Anderson-Fischer et al. | 604/364 |
| 6,107,537 A | 8/2000 | Elder et al. | |
| 6,120,487 A | 9/2000 | Ashton | |
| 6,120,489 A | 9/2000 | Johnson et al. | |
| 6,300,398 B1 | 10/2001 | Jialanella et al. | |
| 6,432,098 B1 | 8/2002 | Kline et al. | |
| 2004/0162536 A1 | 8/2004 | Becker et al. | |
| 2004/0167486 A1 | 8/2004 | Busam et al. | |
| 2005/0177123 A1 | 8/2005 | Catalan | |

FOREIGN PATENT DOCUMENTS

| | | |
|---|---|---|
| WO | WO 95/16746 A1 | 6/1995 |
| WO | WO 97/33921 | 9/1997 |
| WO | WO 97/36564 | 10/1997 |
| WO | WO 01/57153 | 8/2001 |

* cited by examiner

ABSORBENT ARTICLE WITH LOW COLD FLOW CONSTRUCTION ADHESIVE

CROSS-REFERENCE TO RELATED APPLICATIONS

This application claims the benefit of U.S. Provisional Application No. 60/714,188 filed Sep. 2, 2005, which is incorporated by reference.

FIELD OF THE INVENTION

This invention relates to the adhesive material, typically a hot melt adhesive, that is used to assemble components into an absorbent article such as diaper (i. e. the construction adhesive). In particular this invention relates to such absorbent articles assembled using a construction adhesive that has reduced flowability when cold (i. e. at temperatures less than about 40° C.).

BACKGROUND OF THE INVENTION

Users, for example caregivers of infants, rely on disposable absorbent articles to make their lives easier. Disposable absorbent articles, such as adult incontinence articles and diapers, are generally manufactured by combining several components. These components typically include a liquid-permeable topsheet; a liquid-impermeable backsheet attached to the topsheet; and an absorbent core located between the topsheet and the backsheet. When the disposable article is worn, the liquid-permeable topsheet is positioned next to the body of the wearer. The topsheet allows passage of bodily fluids into the absorbent core. The liquid-impermeable backsheet helps prevent leakage of fluids held in the absorbent core. The absorbent core generally is designed to have desirable physical properties, e.g. a high absorbent capacity and high absorption rate, so that bodily fluids can be transported from the skin of the wearer into the disposable absorbent article.

Frequently one or more components of a disposable absorbent article are adhesively bonded together. For example, adhesives have been used to bond individual layers of the absorbent article, such as the topsheet and backsheet together. Adhesives have also been used to bond discrete components, such as fasteners and leg elastics or cuffs, to the article. The adhesive is often called a construction adhesive because it is used to help construct the absorbent article from individual components.

In many instances, a hot-melt adhesive, i.e. a polymeric formulation that is heated to substantially liquefy the formulation prior to application to one or both materials when making a laminate, is used as a construction adhesive. While such formulations generally work, they can be costly and their performance properties can be improved. For example:

It is desirable that the adhesive remain in its intended location after the absorbent article has been assembled and not flow when "cold" (i. e. at normal ambient conditions of less than about 40° C.). Such "cold flow" has been found to result in undesirable adhesion between surfaces of the absorbent article that are not intended to adhere to each other (e. g. a portion of the topsheet in a diaper that has been folded for packaging may adhere to another facing portion of the topsheet).

Such adhesives also have a desirable "open time" (i. e. the time when the hot melt adhesive is at a high enough temperature that it can join one material to another. If open time is too short, the adhesive is not suitable as a construction adhesive because components cannot be reliably assembled. If open time is too long the adhesive may transfer from the assembled components of the absorbent article to components of the production line with resulting hygiene issues.

Thus, there is a continuing need for improved construction adhesives for use in absorbent articles and the production thereof.

SUMMARY OF THE INVENTION

The present invention is a disposable absorbent article that is assembled from a collection of components using a low cold flow construction adhesive. The construction adhesive comprises a polyolefin resin combined with an effective amount of a crystallization enhancer. The Absorbent articles have an in bag compression opening force of less than about 0.75N. The invention also comprises a method of producing the absorbent articles from a low cold flow construction adhesive.

DETAILED DESCRIPTION OF THE INVENTION

Figure 1:
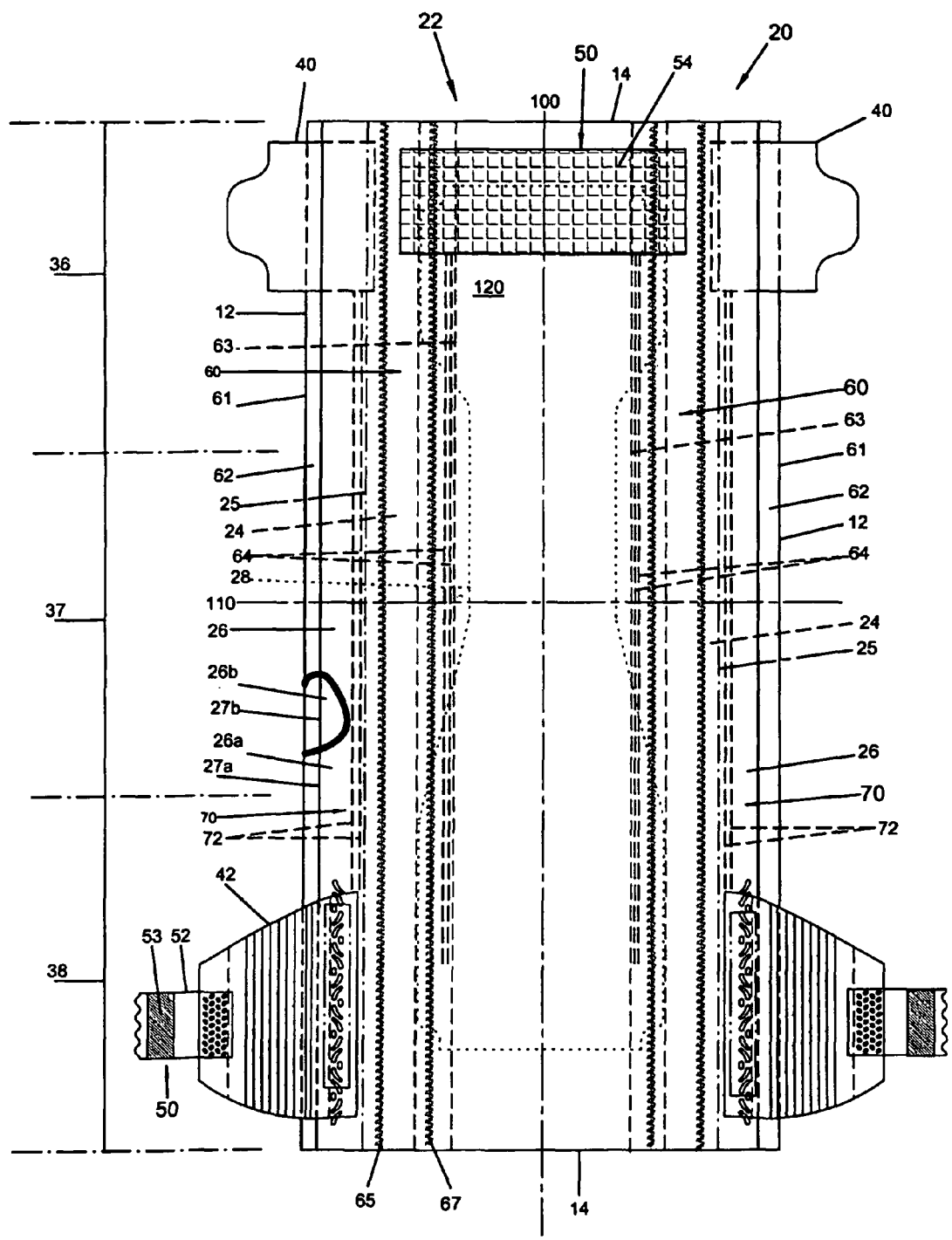
FIG. 1 is a plan view of an exemplary diaper in a flat, uncontracted state.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable." As is well known in the art, a common method for measuring the permeability to water, urine, or synthetic urine of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

"Extendibility" and "extensible" mean that the width or length of the component in a relaxed state can be extended or increased.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties. Elastomeric materials may include elastomeric films, scrims, nonwovens, and other sheet-like structures.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Pant" refers to disposable absorbent articles having a preformed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Nonwoven" fabric or web means a web having a structure of individual fibers or threads that are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note: to convert from osy to gsm, multiply osy by 33.91.)

"Woven" fabric or web means a fabric or web containing a structure of fibers, filaments, or yarns, which are arranged in an orderly, inter-engaged fashion. Woven fabrics typically contain inter-engaged fibers in a warp and fill direction. The warp direction corresponds to the length of the fabric while the fill direction corresponds to the width of the fabric. Woven fabrics can be made, for example, on a variety of looms including, but not limited to, shuttle looms, rapier looms, projectile looms, air jet looms, and water jet looms.

"Spunbonded fibers", or "spunbond fibers", means small-diameter fibers that are typically formed by extruding molten thermoplastic material as filaments from a plurality of fine capillaries of a spinneret having a circular or other configuration, with the diameter of the extruded filaments then being rapidly reduced as by, for example, in U.S. Pat. Nos. 4,340,563, 3,692,618, 3,802,817, 3,338,992, 3,341,394, 3,502,763, 3,502,538, and 3,542,615. Spunbond fibers are quenched and generally not tacky when they are deposited onto a collecting surface. Spunbond fibers are generally continuous and often have average diameters larger than about 7 microns, and more particularly between about 10 and 30 microns. A spunbond material, layer, or substrate comprises spunbonded (or spunbond) fibers.

The term "meltblown fibers" means fibers formed by extruding a molten material, typically thermoplastic in nature, through a plurality of fine, usually circular, die capillaries as molten threads or filaments into converging high-velocity heated gas (e.g., air) streams that attenuate the filaments of molten material to reduce their diameter, which may be to microfiber diameter. Thereafter, the meltblown fibers are carried by the high-velocity gas stream and are deposited on a collecting surface to form a web of randomly dispersed meltblown fibers. Such a process is disclosed for example, in U.S. Pat. No. 3,849,241. Meltblown fibers are microfibers which may be continuous or discontinuous, are generally smaller than 10 microns in diameter, and are generally self-bonding when deposited onto a collecting surface The term "microfibers" means small-diameter fibers having an average diameter not greater than about 100 microns, for example, having a diameter of from about 0.5 microns to about 50 microns, more specifically microfibers may also have an average diameter of from about 1 micron to about 20 microns. Microfibers having an average diameter of about 3 microns or less are commonly referred to as ultra-fine microfibers. A description of an exemplary process of making ultra-fine microfibers maybe found in, for example, U.S. Pat. No. 5,213,881.

"Conventional hot-melt adhesive" means a formulation that generally comprises several components. These components typically include one or more polymers to provide cohesive strength (e.g., aliphatic polyolefins such as poly(ethylene-co-propylene) copolymer; ethylene vinyl acetate copolymers; styrene-butadiene or styrene-isoprene block copolymers; etc.); a resin or analogous material (sometimes called a tackifier) to provide adhesive strength (e.g., hydrocarbons distilled from petroleum distillates; rosins and/or rosin esters; terpenes derived, for example, from wood or citrus, etc.); perhaps waxes, plasticizers or other materials to modify viscosity (i.e., flowability) (examples of such materials include, but are not limited to, mineral oil, polybutene, paraffin oils, ester oils, and the like); and/or other additives including, but not limited to, antioxidants or other stabilizers. A typical hot-melt adhesive formulation might contain from about 15 to about 35 weight percent cohesive strength polymer or polymers; from about 50 to about 65 weight percent resin or other tackifier or tackifiers; from more than zero to about 30 weight percent plasticizer or other viscosity modifier; and optionally less than about 1 weight percent stabilizer or other additive. It should be understood that other adhesive formulations comprising different weight percentages of these components are possible.

"Hot-melt processable" means that an adhesive composition may be liquefied using a hot-melt tank (i.e., a system in which the composition is heated so that it is substantially in liquid form) and transported via a pump (e.g., a gear pump or positive-displacement pump) from the tank to the point of application proximate a substrate or other material; or to another tank, system, or unit operation (e.g., a separate system, which may include an additional pump or pumps, for delivering the adhesive to the point of application). Hot-melt tanks used to substantially liquefy a hot-melt adhesive typically operate in a range from about 38° C. to about 230° C. Generally, at the point of application, the substantially liquefied adhesive composition will pass through a nozzle or bank of nozzles, but may pass through some other mechanical element such as a slot. A hot-melt processable adhesive composition is to be contrasted with a composition that requires a conventional extruder, and the attendant pressures and temperatures characteristic of an extruder, to liquefy, mix, and/or convey the composition. While a hot-melt tank and pump in a hot-melt processing system can handle adhesive-composition viscosities in a range from about 1000 centipoise to about 10,000 centipoise, an extruder can handle and process adhesive-composition viscosities in a range from about 10,000 centipoise to viscosities of several hundred thousand centipoise.

Unless otherwise noted, "Laminated structure" or "laminate" means a structure in which one layer, material, component, web, or substrate is adhesively bonded, at least in part, to another layer, material, component, web, or substrate. As stated elsewhere in this application, a layer, material, component, web, or substrate may be folded over and adhesively bonded to itself to form a "laminated structure" or "laminate."

FIG. 1 is a plan view of an exemplary, non-limiting embodiment of a diaper 20 of the present invention in a flat, uncontracted state (i.e., without elastic induced contraction). The garment-facing surface 120 of the diaper 20 is facing the viewer. The diaper 20 includes a longitudinal centerline 100 and a lateral centerline 110. The diaper 20 may comprise a chassis 22. The diaper 20 and chassis 22 are shown to have a front waist region 36, a rear waist region 38 opposed to the front waist region 36, and a crotch region 37 located between the front waist region 36 and the rear waist region 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The outer periphery of chassis 22 is defined by longitudinal side edges 12 and end edges 14. The chassis 22 may have opposing longitudinal side edges 12 that are oriented generally parallel to the longitudinal centerline 100. However, for better fit, longitudinal side edges 12 may be curved or angled to produce, for example, an "hourglass" shape diaper when viewed in a plan view. The chassis 22 may have opposing lend edges 14 that are oriented generally parallel to the lateral centerline 110.

The chassis 22 may comprises a liquid permeable topsheet 24 having longitudinal side edges 25, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the diaper 20 with other features may added to form the composite diaper structure. While the topsheet 24, the backsheet 26, and the absorbent core 28 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 24 is generally a portion of the diaper 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. A particularly preferred topsheet 24 is available from BBA Fiberweb, Brentwood, Tenn. as supplier code 055SLPV09U.

Any portion of the topsheet 24 may be coated with a lotion as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. These materials may be combined to provide a core 28 in the form of one or more layers (individual layers not shown) that may include fluid handling layers such as acquisition layers, distribution layers and storage layers. Such absorbent cores 28 may also include layers (not shown) to stabilize other core components. Such layers include a core cover and a dusting layer. A suitable material for such layers is a spunbonded/meltblown/spunbonded nonwoven having a basis weight between about 10 and 15 $g/m^2$ (the meltblown layer comprises <5 $g/m^2$) as is available from Avgol America, Inc. of Knoxville, N.C. For example, Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222 and in published U.S. patent application Ser. Nos. 04/0,162,536 and 04/0,167,486.

The backsheet 26 is generally positioned such that it may be at least a portion of the garment-facing surface 120 of the diaper 20. Backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer, as illustrated in the cut-away of FIG. 1. The backsheet 26 may comprise an outer cover 26a and an inner layer 26b. The outer cover 26a may have longitudinal side edges 27a and the inner layer 26b may have longitudinal side edges 27b. The outer cover 26a may be made of a soft, non-woven material. The inner layer 26b may be made of a substantially water-impermeable film. The outer cover 26a and an inner layer 26b may be joined together by adhesive or any other suitable material or method. A particularly suitable outer cover 26a is available from Corovin GmbH, Peine, Germany as supplier code A18AH0, and a particularly suitable inner layer 26b is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

The diaper 20 may also include a fastening system 50. When fastened, the fastening system 50 interconnects the front waist region 36 and the rear waist region 38 resulting in a waist circumference that may encircle the wearer during wear of the diaper 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

FIG. 1 depicts a fastening system 50 having an engaging member 52 and a receiving member 54. The engaging member 52 is shown having an engaging surface 53 that may comprise hooks, loops, an adhesive, a cohesive, or other fastening member. The receiving member 54 may have a surface that allows for engagement of the engaging member 52. The receiving member 54 may comprise hooks, loops, an adhesive, a cohesive, or other fastening component that can receive the engaging member 52. Suitable engaging member 52 and receiving member 54 combinations include but are not limited to hooks/loop, hooks/hooks, adhesive/polymeric film; cohesive/cohesive, adhesive/adhesive; tab/slot; and button/button hole.

The diaper 20 may include barrier cuffs 60 and/or gasketing cuffs 70. Gasketing cuffs 70 may also be referred to as outer leg cuffs, leg bands, side flaps, leg cuffs, or elastic cuffs. Barrier cuffs 60 may also be referred to as second cuffs, inner leg cuffs or "stand-up" elasticized flaps.

The gasketing cuff 70 may be substantially inelastic or may be elastically extensible to dynamically fit at the wearer's leg. The gasketing cuff 70 may be formed by one or more elastic members 72 (such as elastic strands) operatively joined to the topsheet 24, backsheet 26, or any other suitable substrate used in the formation of the diaper 20. Suitable gasketing cuff construction is further described in U.S. Pat. No. 3,860,003

The barrier cuff 60 may have a distal edge 61 and a proximal edge 63 that run substantially parallel to the longitudinal centerline 100. The barrier cuff 60 may span the entire longitudinal length of the diaper 20. The barrier cuff 60 may be formed by a flap 62 and an elastic member 64 (such as elastic strands). The flap 62 may be a continuous extension of any of the existing materials or elements that form the diaper 20. In other embodiments, such as shown in FIG. 1, the barrier cuff 60 may be a discrete element. In such embodiments, the barrier cuff 60 comprising the flap 62 and the elastic member 64 may be formed then joined to the chassis 22 by a bond 65.

The flap 62 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the flap 62 may comprise a nonwoven web such as spunbond webs, meltblown webs, carded webs, and combinations thereof (e.g., spunbond-meltblown composites and variants). Laminates of the aforementioned substrates may also be used to form the flap 62. A particularly suitable flap may comprise a nonwoven available from BBA Fiberweb, Brentwood, Tenn. as supplier code 30926. A particularly suitable elastic member is available from Invista, Wichita, Kans. as supplier code T262P. Further description of diapers having barrier cuffs and suitable construction of such barrier cuffs may be found in U.S. Pat. Nos. 4,808,178 and 4,909,803. The elastic member 64 generally spans the longitudinal length of the barrier cuff 60. In other embodiments, the elastic member 64 may span at least the longitudinal length of the barrier cuff 60 within the crotch region 37. It is desirable that the elastic member 64 exhibits sufficient elasticity such that the proximal edge 63 of the barrier cuff 60 remains in contact with the wearer during normal wear, thereby enhancing the barrier properties of the barrier cuff 60. The elastic member 64 may be connected to the flap 62 at opposing longitudinal ends. In certain embodiments, the flap 62 may be folded over onto itself so as to encircle the elastic member 64. A bond 67 may be used to secure the folded section of the flap 62.

The barrier cuffs 60 and/or gasketing cuffs 70 may be treated, in full or in part, with a lotion, as described above with regard to topsheets, or may be fully or partially coated with a hydrophobic surface coating as detailed in U.S. application Ser. No. 11/055,743, which was filed Feb. 10, 2005.

The diaper 20 may include front ears 40 and back ears 42. The front and/or back ears 40, 42 may be unitary elements of the diaper 20 (i.e., they are not separately manipulative elements secured to the diaper 20, but rather are formed from and are extensions of one or more of the various layers of the diaper). In certain embodiments, the front and/or back ears 40, 42 may be discrete elements that are joined to the chassis 22, as shown in FIG. 1. Discrete front and/or back ears 40, 42 may be joined to the chassis 22 by any bonding method known in the art such as adhesive bonding, pressure bonding, heat bonding, and the like. In other embodiments, the front and/or back ears 40, 42 may comprise a discrete element joined to the chassis 22 with the chassis 22 having a layer, element, or substrate that extends over the front and/or back ear 40, 42. The front ears 40 and back ears 42 may be extensible, inextensible, elastic, or inelastic. The front ears 40 and back ears 42 may be formed from nonwoven webs, woven webs, knitted fabrics, polymeric and elastomeric films, apertured films, sponges, foams, scrims, and combinations and laminates thereof. In certain embodiments the front ears 40 and back ears 42 may be formed of a nonwoven/elastomeric material laminate or a nonwoven/elastomeric material/nonwoven laminate. A suitable elastic back ear 42 may be a laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332). While the following embodiments are directed to back ear 42 design and construction, these embodiments are equally applicable to front ear 40 design and construction. It should be recognized that any combination of the following embodiments may be used for the back ear 42 and/or the front ear 40.

In alternative embodiments, the diaper 20 may be preformed by the manufacturer to create a pant. A pant may be preformed by any suitable technique including, but not limited to, joining together portions of the article using refastenable and/or non-refastenable bonds (e.g., seam, weld, adhesive, cohesive bond, fastener, etc.). For example, the diaper 20 of FIG. 1 may be manufactured with the fastening system 50 engaged (i.e., the engaging member 52 is joined to the receiving member 54). As an additional example, the diaper 20 of FIG. 1 may be manufactured with the front ears 40 joined to the back ears 42 by way of a bond such as an adhesive bond, a mechanical bond, or some other bonding technique known in the art. Suitable pants are disclosed in U.S. Pat. Nos. 5,246,433; 5,569,234; 6,120,487; 6,120,489; 4,940,464; 5,092,861; 5,897,545; and 5,957,908.

As noted above, a construction adhesive is typically used to join components of an absorbent article as the absorbent article is being assembled. Nonlimiting examples of such joinder using the construction adhesive include but are not limited to:
core cover to dusting layer sealing;
backsheet 26 to core 28;
elastic member 64 to nonwoven and/or film to form a barrier cuff 60 or a gasketing cuff 70.
nonwoven to vapor permeable film to form a backsheet 26;
barrier cuffs to topsheet 24;
receiving member 54 to topsheet 24;
ear 40, 42 to backsheet 26.

As will be recognized, many of these uses involve joinder of a nonwoven material to another material. As will be further recognized, if the construction adhesive is too fluid for the time scale of the operation, it can flow through the nonwoven material with deleterious effect on process performance or product perception.

In one example, if the open time of the construction adhesive is too long, the adhesive may remain flowable and tacky after the two components to be joined have passed from the joinder unit operation on the assembly process to a subsequent unit operation in the process. In some instances such a downstream process may put a force on the adhesive causing it to flow through the nonwoven material. For example, if the nonwoven material passes over a roll, web tension can cause pressure on the nonwoven causing a flowable adhesive to flow into and even through void space in the nonwoven. If the adhesive reaches the surface of the nonwoven that contacts the roll portion of the adhesive can transfer to the roll with resulting contamination thereof. Such contamination can cause substantial operational problems (e.g. roll wrapping) to a web based assembly process.

In another example, if the viscosity at ambient conditions (e.g. less than about 40° C.) is too low the pressure caused by the compression packaging typically used for absorbent articles can provide a driving force to cause a portion of the construction adhesive to flow into and even through the void volume of a nonwoven material (It should be recognized that too low is a relative term and the absolute viscosity can be quite high and still flow into a nonwoven due to the relatively long time scale). If the adhesive reaches an outer surface of the nonwoven material it can act to join any adjacent material thereto. For example, the construction adhesive (not shown) used to join the elastic member 64 of barrier cuff 60 to the nonwoven material comprising flap 62 may flow through the nonwoven material causing barrier cuff 60 to adhere to topsheet 24. If such adherence occurs a user (e. g. a caregiver for an infant) may have difficulty opening the diaper for application to a wearer. The In Bag Compression Opening Test described in the TEST METHODS section below simulates the opening of an absorbent article for use and provides a measure of any force causing components of the absorbent article to adhere to each other with a resulting increase in opening difficulty.

It has been surprisingly found that increasing the crystallization rate of the polymeric material comprising the construction adhesive provides an unexpected reduction in such opening force. As can be seen from the EXAMPLE below and in FIG. 2, adding an effective amount of a crystallization facilitator can provide a marked decrease in the product opening force as measured by the In Bag Compression Opening Test. As used herein an effective amount of a crystallization enhancer is the quantity required to cause the opening force of a product assembled using a construction adhesive comprising the crystallization enhancer to be less than 0.75N as measured by the In Bag Compression Opening Test. Preferably, the opening force is less than about 0.6N, more preferably less than about 0.5N. Suitable crystallization enhancers include, but are not limited to, microcrystalline waxes and crystalline olefin homopolymers. Particularly preferred is a linear polyethylene homopolymer. Without being bound by theory it is believed that such materials crystallize more readily as temperature decreases due to minimal branching. The crystallites thus formed then serve as a template for crystallization of the polymeric material.

As is known, hot melt adhesives can comprise a wide variety of base polymers. Suitable materials for formulation of hot melt adhesives include, but are not limited to polyethylene; ethylene vinyl acetate; block copolymer elastomers (e.g. styrene-isoprene-styrene (SIS) and styrene-butadiene-styrene (SBS)) and amorphous polyolefins (e.g. atactic polypropylene). Hot melt adhesives formulated from some of these base polymers can even have a desirably low opening force. For example, the styrene-isoprene-styrene based hot melt formulation (H1358 as is available from H. B. Fuller Company of St. Paul, Minn.) described in the EXAMPLE has an opening force of about 0.5N. However, the susceptibility of block copolymer based adhesives to oxidation is well known (Without being bound by theory such susceptibility is believed to be due to residual unsaturation in the polymer backbone which is susceptible to degradation). Preferred hot melt adhesives for purposes the present invention are those formulations based on an ethylene interpolymer with a $C_3$-$C_{20}$ α olefin as are generally described in published PCT application WO 97/33921. Particularly preferred resin comprising such polymers are interpolymers of ethylene and 1-octene marketed by the Dow Chemical Company of Midland, Mich. under the trade name Affinity. Such formulations provide desirable oxidation resistance because they are believed to have less residual unsaturation and can be modified by appropriate choice of a crystallization enhancer so as to provide absorbent articles having the low opening force of the present invention. A particularly preferred hot melt adhesive formulation for use as a construction adhesive to provide absorbent articles according to the present invention is D3166 as is available from H. B. Fuller Company.

The construction adhesive can be applied using a wide variety of known application methods including but not limited to slot extrusion, sprays, including spiral sprays, and beads. Specific examples include but are not limited to:
- application of the construction adhesive in a spiral spray or slot coating to join a topsheet to an underlying nonwoven layer;
- application of the construction adhesive via slot coating to join an acquisition layer or a distribution layer to a core cover;
- application of beads of the construction adhesive located between the nonwoven material comprising the cuff and the backsheet;
- application of the construction adhesive in a spiral spray or slot coating to join the topsheet to the backsheet so as to seal the longitudinal edges of the absorbent article;
- application of the construction adhesive using slot coating to join a landing zone (i.e. a receiving member) to the backsheet;
- application of the construction adhesive using slot coating to join the core cover to the dusting layer;
- application of the construction adhesive in a spiral spray to join the core to the backsheet.
- application of the construction adhesive in a spiral spray to join the nonwoven material comprising the cuff to the nonwoven material comprising the backsheet.

In order to be hot melt processable so as to enable application of the construction adhesive, the adhesive must be heated to a temperature high enough so as to insure the adhesive flows readily but not so hot as to cause degradation of the adhesive at an unacceptable rate. Suitably, the adhesive is maintained at a temperature between about 100° C. and about 230° C. before application. Preferably the adhesive is maintained at a temperature between about 120° C. and about 200° C.

Test Methods

In Bag Compression Opening Force Test
Sample Preparation
1. Assemble finished absorbent articles using the construction adhesive to be evaluated and pack into commercially sized packaging.
2. Store the packed absorbent articles at 60° C.±2° C. for 3 days using a suitable means (e.g. a laboratory oven.
3. Remove the packed absorbent articles from 60° C. storage and allow to equilibrate at 25° C.±2° C.
4. Open the packaging and carefully remove at least 5 absorbent articles per evaluation therefrom taking care not to disturb any bonding between surfaces.

Opening Force Measurement
Apparatus
Tensile Tester: A suitable instrument is available from MTS Systems of Eden Prairie Minn. as a model Q Test/1L or equivalent
Load Cell: 100N; MTS Part No. 450100818
Jaws: 25×75 mm with rubber grips; MTS Part No. 56-163-815 or equivalent
Interface Software: Test Works 4 from MTS or equivalent. Set up to acquire force/extension data from the tensile tester.
Personal Computer: Suitable system for running the interface software
Setup
Crosshead Speed 300 mm/min
Gage Length 60 mm
Stop Length 120 mm
Operation
1. Set up and calibrate the tensile tester according to the manufacturer's instructions.
2. Carefully unfold any longitudinal folds so as to expose one of the ears of the sample absorbent article.
3. Partially unfold, insert and clamp the distal edge of the ear of the sample into the upper jaw taking care not to disturb any adhesion that may be present between components of the absorbent article.
4. Carefully insert and clamp the folded opposing ear into the lower jaw of the tensile tester insuring that there is slight slack in the clamped sample.
5. Initiate the extension cycle of the tensile tester
6. The opening force is defined as the peak force observed during the 60 mm extension cycle.
7. Repeat steps 2-6 for at least 4 additional samples.
Calculation And Reporting
1. Determine the average and standard deviation of the individual opening forces measured as described above.
2. Report the mean opening force for each absorbent article type evaluated and the related standard deviation.

EXAMPLE

This example is intended to show the mean opening force for construction adhesives used to assemble absorbent articles.

Infant diapers were produced on a standard diaper production line using three different construction adhesives. Table 1 describes the adhesives and the results of opening force evaluation.

TABLE 1

In Bag Compression Opening Force for Various Construction Adhesives

| | Construction Adhesive Type | | |
|---|---|---|---|
| | A<br>Polyolefin Based<br>Not of the<br>Invention[1] | B<br>Polyolefin Based<br>According to the<br>Invention[2] | C<br>SIS Based[3] |
| Mean | 1.2N | 0.5N | 0.5N |
| Standard Deviation | 0.47N | 0.10N | 0.11N |

Figure 2:
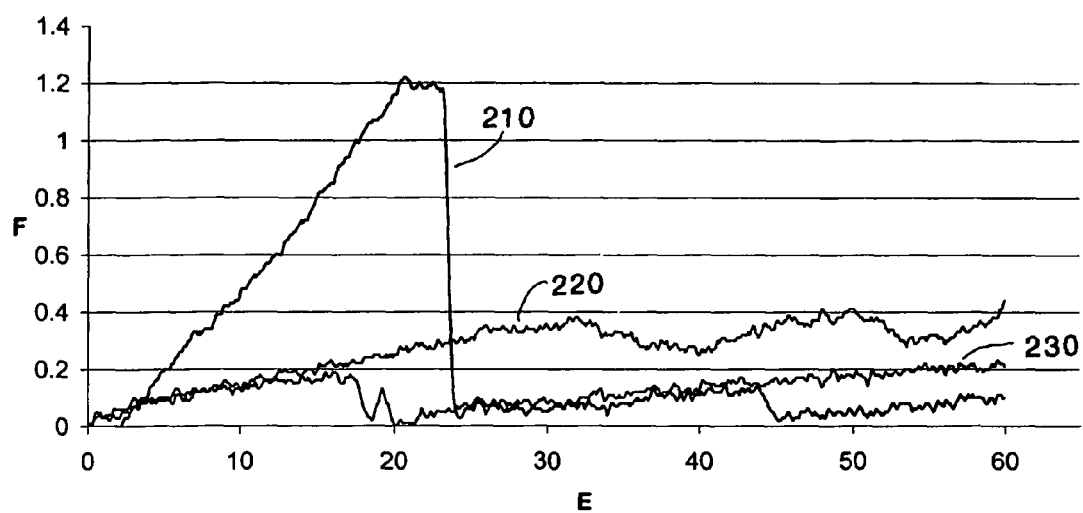
FIG. 2 is a stress/strain curve of opening force for the absorbent articles of the Example.

[1]Size 5 infant diaper assembled using construction adhesive D3155 as is available from H. B. Fuller Company of St. Paul, MN
[2]Size 5 infant diaper assembled using construction adhesive D3166 as is available from H. B. Fuller Company of St. Paul, MN
[3]Size 4 infant diaper assembled using construction adhesive H1358LOF as is available from H. B. Fuller Company of St. Paul, MN FIG. 2 shows a representative stress strain curve (F is force in Newtons and E is extension in mm) for measurement of the opening force for a diaper assembled using each of the construction adhesives where 210 is the curve for adhesive A, 220 is the curve for adhesive B and 230 is the curve for adhesive C. As can be seen the construction adhesive used to assemble diapers according to the present invention and the diapers assembled using the SIS construction adhesive have very comparable mean opening forces while the diapers assembled using the other polyolefin based adhesive has an opening force nearly three times as large.

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It should be apparent that combinations of such embodiments and features are possible and can result in executions within the scope of this invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm.

All documents cited in the Detailed Description of the invention are, in relevant part, incorporated herein by reference; the citation of any document is not to be construed as an admission that it is prior art with respect to the present invention.

What is claimed is:

1. A disposable absorbent article comprising
   a) a topsheet;
   b) a backsheet underlying said topsheet;
   c) an absorbent core disposed between said topsheet and said backsheet; and
   d) a polyolefin-based, low cold flow construction adhesive suitable for joining at least two absorbent article components together, wherein said adhesive comprises an ethylene-based polyolefin resin and a crystallization enhancer, and wherein said absorbent article has an in bag compression opening force of less than about 0.75N.

2. The disposable absorbent article according to claim 1, wherein said opening force is less than about 0.6N.

3. The disposable absorbent article according to claim 2, where said opening force is less than about 0.5N.

4. The absorbent article according to claim 1, wherein said polyolefin-based, low cold flow construction adhesive joins said topsheet to an underlying nonwoven layer.

5. The absorbent article according to claim 1, wherein said polyolefin-based, low cold flow construction adhesive joins an elastic material to a nonwoven material to form a barrier cuff 6. The absorbent article according to claim 1, wherein said polyolefin-based, low cold flow construction adhesive joins an elastic material to said backsheet.

7. The absorbent article according to claim 1, wherein said polyolefin-based, low cold flow construction adhesive joins an acquisition layer to a core cover.

8. The absorbent article according to claim 1, wherein said polyolefin-based, low cold flow construction adhesive joins a distribution layer to said core cover.

9. The absorbent article according to claim 1, wherein said polyolefin-based, low cold flow construction adhesive joins said topsheet to said backsheet adjacent a longitudinal edge of said absorbent article.

10. The absorbent article according to claim 1, wherein said polyolefin-based, low cold flow construction adhesive joins a receiving member to said backsheet.

11. The absorbent article according to claim 1, wherein said polyolefin-based, low cold flow construction adhesive joins a core cover to a dusting layer.

12. The absorbent article according to claim 1, wherein said polyolefin-based, low cold flow construction adhesive joins a core cover to said backsheet.

13. The absorbent article according to claim 1, wherein said polyolefin-based, low cold flow construction adhesive joins a dusting layer to said backsheet.

14. The absorbent article according to claim 1, wherein the absorbent article is a diaper.

15. The method according to claim 1, wherein said ethylene-based polyolefin resin comprises an ethylene interpolymer with a $C_3$-$C_{20}$ α olefin.

16. A method of assembling an absorbent article comprising the steps of:
   a) providing a polyolefin-based, low cold flow construction adhesive wherein said adhesive comprises an ethylene-based polyolefin resin and a crystallization enhancer;
   b) providing a plurality of absorbent article components; and
   c) joining at least one of said absorbent article components to another of said absorbent article components using said polyolefin-based, low cold flow construction adhesive so as to assemble said absorbent article whereby said absorbent article has an in bag compression opening force of less than about 0.75N.

17. The method according to claim 16, wherein step c comprises the step of joining a topsheet to an underlying nonwoven layer.

18. The method according to claim 16, wherein step c comprises the step of joining an elastic material to a nonwoven material to form a barrier cuff 19. The method according to claim 16, wherein step c comprises the step of joining an elastic material to a nonwoven and backsheet materials.

20. The method according to claim 16, wherein step c comprises the step of joining an acquisition layer to a core cover.

21. The method according to claim 16, wherein step c comprises the step of joining a distribution layer to a core cover.

22. The method according to claim 16, wherein step c comprises the step of joining a topsheet to a backsheet adjacent a longitudinal edge of said absorbent article.

23. The method according to claim 16, wherein step c comprises the step of joining a receiving member to a backsheet.

24. The method according to claim 16, wherein step c comprises the step of joining a core cover to a dusting layer.

25. The method according to claim 16, wherein step c comprises the step of joining a core to a backsheet.

26. The method according to claim 16, wherein step c comprises the step of joining a dusting layer to a backsheet.

27. The method according to claim 16, wherein said absorbent article has an opening force of less than about 0.6N.

28. The method according to claim 16, wherein said opening force is less than about 0.5N.

29. The method according to claim 16, wherein the absorbent article is a diaper.

30. The method according to claim 16, wherein said ethylene-based polyolefin resin comprises an ethylene interpolymer with a $C_3$—$C_{20}$ α olefin.

* * * * *